United States Patent
Hanson et al.

(10) Patent No.: US 10,933,192 B2
(45) Date of Patent: Mar. 2, 2021

(54) ASEPTIC CONNECTIONS FOR DRUG DELIVERY DEVICES

(71) Applicant: UNL Holdings LLC, New York, NY (US)

(72) Inventors: Ian B. Hanson, Wayne, PA (US); Lawton Laurence, Phoenixville, PA (US); Antonio Ubach, Tucson, AZ (US)

( * ) Notice: Subject to any disclaimer, the term of this patent is extended or adjusted under 35 U.S.C. 154(b) by 312 days.

(21) Appl. No.: 15/885,404

(22) Filed: Jan. 31, 2018

(65) Prior Publication Data

US 2018/0221573 A1 Aug. 9, 2018

Related U.S. Application Data

(60) Provisional application No. 62/452,705, filed on Jan. 31, 2017.

(51) Int. Cl.
*A61M 5/162* (2006.01)
*A61M 5/142* (2006.01)
*A61J 1/14* (2006.01)

(52) U.S. Cl.
CPC ............ *A61M 5/162* (2013.01); *A61J 1/1406* (2013.01); *A61J 1/1412* (2013.01);
(Continued)

(58) Field of Classification Search
CPC .............. A61M 5/162; A61M 5/14248; A61M 25/0111; A61J 1/1412; A61J 1/2089; A61J 1/2096
(Continued)

(56) References Cited

U.S. PATENT DOCUMENTS

2013/0253472 A1* 9/2013 Cabiri ............... A61M 5/14566
604/506
2014/0148784 A1 5/2014 Anderson et al.
(Continued)

FOREIGN PATENT DOCUMENTS

WO WO 2015/199981 A1 12/2015
WO WO 2016/048878 A1 3/2016
(Continued)

OTHER PUBLICATIONS

Notification Concerning Transmittal of the International Preliminary Report on Patentability of International Application No. PCT/IB2018/000049, entitled: "Aseptic Connections for Drug Delivery Devices," dated Aug. 13, 2020.
(Continued)

*Primary Examiner* — Brandy S Lee
*Assistant Examiner* — Nidah M Hussain
(74) *Attorney, Agent, or Firm* — Hamilton, Brook, Smith & Reynolds, P.C.

(57) ABSTRACT

Devices and methods for establishing aseptic connections between a drug container and a fluid pathway connection for a drug pump are provided. A fluid pathway connection includes a connection hub, a piercing member, a piercing member retainer, and a drug container. The drug container includes a cap, a pierceable seal, and a barrel. The piercing member is at least partially disposed in a sterile chamber defined by the connection hub, and the connection hub is configured to be connected to the drug container while maintaining an aseptic condition of a fluid pathway from the sterile chamber to an interior of the drug container.

21 Claims, 13 Drawing Sheets

(52) U.S. Cl.
CPC ..... *A61M 5/14248* (2013.01); *A61M 2205/18* (2013.01); *A61M 2205/3317* (2013.01); *A61M 2205/50* (2013.01); *A61M 2205/581* (2013.01); *A61M 2205/587* (2013.01); *A61M 2207/00* (2013.01)

(58) Field of Classification Search
USPC .......................................................... 604/151
See application file for complete search history.

(56) References Cited

U.S. PATENT DOCUMENTS

2015/0359965 A1    12/2015   O'Connor et al.
2016/0082182 A1*   3/2016    Gregory ............ A61M 5/14526
                                                          604/150

FOREIGN PATENT DOCUMENTS

| WO | WO 2016/141082 A1 | 9/2016 |
| WO | WO 2017/139741 A1 | 8/2017 |
| WO | WO 2017/177094 A2 | 10/2017 |
| WO | WO 2019/150145 A1 | 8/2019 |

OTHER PUBLICATIONS

Notification of Transmittal of the International Search Report and the Written Opinion of International Application No. PCT/IB2018/000049, entitled: "Aseptic Connections for Drug Delivery Devices," dated Jun. 22, 2018.

* cited by examiner

ASEPTIC CONNECTIONS FOR DRUG DELIVERY DEVICES

RELATED APPLICATION

This application claims the benefit of U.S. Provisional Application No. 62/452,705, filed on Jan. 31, 2017. The entire teachings of the above application are incorporated herein by reference.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable rate delivery. These infusion capabilities usually result in better efficacy of the drug and therapy and less toxicity to the patient's system. Currently available ambulatory infusion devices are expensive, difficult to program and prepare for infusion, and tend to be bulky, heavy, and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients and healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injection pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

There is a strong market demand for drug delivery devices which are easy-to-use, cost-efficient, and which include integrated safety features. However, manufacturing of such devices can be cost intensive, which results in higher costs to patients. Much of the manufacturing costs can be attributed to the need to maintain a sterile fluid pathway from the drug container to the needle, prior to introduction of the drug to the patient. Some commercial products seek to maintain the sterility of the device by manufacturing the components in a non-sterile environment and then sterilizing the entire device. A recognized downside of such processes is the need to separately fill the drug container after the device sterilization but prior to drug injection, as most pharmaceutical compounds are not capable of withstanding the device sterilization process. Alternatively, the drug delivery device may be manufactured as a pre-filled device, wherein the device is filled with the drug aseptically during assembly. Such manufacturing processes may be costly since the entire process must be kept sterile and because the fill and assembly lines need to be specially-tailored for the device. Accordingly, this adds substantial operating costs to pharmaceutical companies and contract drug-fillers.

Drug delivery devices are generally prepared by molding or shaping the various components and then assembling the components. The assembling steps and other processing operations typically produce a device that subsequently must be cleaned to remove particulates adhering to the surfaces to satisfy cleanliness standards for drug delivery devices. After cleaning, conventional drug delivery devices are packaged and sterilized. Such delivery devices have been classified into several general types. The first type is assembled and placed in sterile packaging which can be shipped with a vial or ampoule of a drug or other injectable solution. The vial or ampoule is generally made of glass or other clear material that does not interfere with the stability of the drug during prolonged storage. The delivery device is filled with the drug or other solution at the point of use and injected into the patient. These devices have the disadvantage of increasing the time and difficulty of filling the device at the point of use with increased possibility of contamination of the delivery device and/or drug solution. There is a further risk of glass particles from the ampoules contaminating the drug solution when the ampoules are opened.

Several of these disadvantages are overcome by providing prefilled delivery devices which can be filled with a suitable drug solution prior to use. Prefilled delivery devices, as the term is known in the art, are devices that are filled by the drug manufacturer and shipped to the health care provider or self-administering patient in a condition that is ready for use. Prefilled delivery devices have the advantage of convenience and ease of application with reduced risk of contamination of the drug solution. Prefilled drug delivery devices are generally assembled and packaged in clean rooms to maintain proper cleanliness levels. The clean rooms are equipped with extensive filter assemblies and air control systems to remove particulates and pyrogens from the air in the room and to prevent particulates and pyrogens from entering the room. The operators and other personnel in the clean room are required to wear appropriate protective garments to reduce contamination of the air and the drug delivery devices being manufactured or assembled. As people and equipment enter and leave the clean room, the risk of contamination and introduction of foreign particulates and pyrogens increases. Various operations are able to form clean and sterile drug delivery devices. However, subsequent handling, filling and printing of the drug delivery device can contaminate the device. It is then necessary to clean and sterilize such conventional drug delivery devices before use. Accordingly, there is a continuing need in the industry for an improved system for manufacturing and assembling clean and sterile medical devices and filling such devices.

SUMMARY

The present invention provides devices and methods for establishing aseptic connections between two or more components or subassemblies. The devices may be used in medical devices such as drug delivery pumps. In some embodiments, a connection is made between a drug container and a fluid pathway connection. The drug container may hold a fluid drug and include a pierceable seal. The fluid pathway connection may include a connection hub, a piercing member, and a retainer. The fluid pathway connection may further include at least one seal that maintains an aseptic condition of at least a portion of the fluid pathway connection. After connection of the fluid pathway connection and upon user initiation, the piercing member may be caused to pierce the pierceable seal to open a fluid pathway for delivery of the fluid drug to a patient.

A fluid pathway connection includes a connection hub, a piercing member, and a piercing member retainer. The piercing member is at least partially disposed in a sterile chamber defined by the connection hub. The fluid pathway connection can further include, or be configured to engage with, a drug container that includes a cap, a pierceable seal, and a barrel. The connection hub is configured to be connected to the drug container while maintaining an aseptic condition of a fluid pathway from the sterile chamber to an interior of the drug container.

The connection hub can define a bore that is configured to receive the pierceable seal of the drug container. The bore can further initially include a seal that is configured to maintain an aseptic condition of the bore. The seal can be configured to be displaced by the pierceable seal. For example, the seal can be a plug seal initially disposed within the bore or a film seal initially disposed at an opening of the bore. One or more seals can be included at each opposing end of the bore. Thus, an interior surface of the bore can be maintained in an aseptic state until the seal is directly displaced by the pierceable seal or, alternatively, by a component of the drug container cap.

The drug container can further include a sliding seal, such as a toroidal seal, that is initially sealing engaged with at least a portion of the pierceable seal. The sliding seal can translate upon the pierceable seal upon connection of the connection hub with the drug container. The pierceable seal can include at least one circumferential rib configured to retain the sliding seal in an initial position. Thus, an exterior surface of the pierceable seal can be maintained in an aseptic state until the sliding seal is directly displaced by the connection hub.

The piercing member retainer can be translatable with respect to the connection hub such that, upon translation of the piercing member retainer, the piercing member is configured to pierce the pierceable seal. The initial location of the sliding seal at the drug container can maintain an aseptic condition of the location at which the piercing member contacts the outer surface of the pierceable seal. The fluid pathway connection can, thus, be configured such that the piercing member, upon activation, travels through locations at which both the pierceable seal and the bore are aseptically maintained.

The fluid pathway connection can include further elements for securing the connection hub to the drug container and/or to the drug container cap. For example, the cap can include at least one locking arm configured to engage with the connection hub. Alternatively, or in addition, the connection hub can include at least one locking arm configured to engage with the cap.

Another fluid pathway connection includes a connection hub that includes a first rotating disk and a drug container that includes a cap and a barrel. The cap includes a second rotating disk, and the connection hub is configured to be connected to the drug container while maintaining an aseptic condition of a fluid pathway from a chamber defined by the connection hub to an interior of the drug container.

The first rotating disk can include a first opening of the fluid pathway connection and the second rotating disk can include a second opening of the fluid pathway connection. The first and second openings can be configured to align upon connection of the connection hub to the drug container. The connection hub can further include a third opening that is initially sealed by the first rotating disk. Similarly, the cap can include a fourth opening that is initially sealed by the second rotating disk. Thus, both the third and fourth openings can be aseptically maintained by the sliding disks. Upon rotation of the first and second disks, the first, second, third, and fourth openings can align, providing for a fluid pathway form the chamber of the connection hub to the interior of the drug container. Optionally, the first and/or second openings include a film seal that can be removed prior to connection and rotation of the disks. Alternatively, or in addition, the fourth opening is defined by a chimney that is configured to translate through the first and second openings upon their alignment with the fourth opening, such that a drug flowing through the fluid pathway is prevented from containing an interior surface of the first and second openings. The chimney can be, for example, spring-loaded, such that its translation occurs automatically upon alignment of the first, second, third, and fourth openings. Thus, the chimney can maintain an aseptic condition of the fluid pathway by blocking exposure of the inner walls of the first and second openings to a fluid travelling through the fluid pathway.

To provide for ease of connection, at least one of the first and second rotating disks can include a post and the other of the first and second rotating disks can include a complementary recess. Optionally, the fluid pathway connection includes a piercing member and a piercing member retainer. When at least one of the openings (e.g., first, second, third, or fourth opening) includes a seal, the piercing member can be configured to pierce the seal upon translation of the piercing member retainer. The seal(s) can thus provide an additional feature to ensure that a fluid pathway defined by the fluid pathway connection is maintained in an aseptic condition throughout connection to a drug container.

A drug delivery pump includes a housing, an activation mechanism, a power and control system, a drive mechanism and a fluid pathway connection. The drug delivery pump can include an assembly platform upon which any or all of the activation mechanism, power and control system, drive mechanism, and fluid pathway connection are mounted. The fluid pathway connection can be in fluid communication with a fluid conduit, the fluid pathway connection and the fluid conduit defining a sterile fluid path from the sterile fluid pathway connection to the insertion mechanism.

A method of assembling the fluid pathway connection includes aligning a bore of the connection hub with a pierceable seal of the drug container and translating the connection hub onto the cap of the drug container. A seal of the connection hub can thus be displaced by the pierceable seal. Where the seal of the connection hub is a plug seal, the translation of the connection hub onto the cap can thus include displacing the plug seal from the bore of the connection hub. Where the seal of the connection hub is a film seal, the translation of the connection hub onto the cap can thus include displacing the film seal from an opening of the bore of the connection hub.

The method can further include displacing a sliding seal located at the pierceable seal. Upon connection, the piercing member retainer can be configured to translate, such that the piercing member pierces the pierceable seal.

Another method of assembling the fluid pathway connection includes aligning a first opening of a first rotating disk of a connection hub with a second opening of a second rotating disk of a cap of the drug container. The method further includes rotating the first and second rotating disks to align the first and second openings with a third opening at the connection hub and a fourth opening at the cap.

The method can further include translating a chimney defining the fourth opening through the first and second openings such that an aseptic condition is maintained, even where the first and second openings are not sealed, such as by a film seal. The chimney can be, for example, spring-loaded, such that its translation occurs automatically upon rotation of the disks to a position that causes the first through fourth openings to align.

The drug container may contain a drug fluid for delivery. The fluid pathway connection may further be in fluid communication with a conduit that provides a fluid pathway for delivery of the fluid drug to the patient. Upon initiation by the user, the fluid drug is delivered through the fluid pathway to the body of the user. The pierceable seal includes a seal barrier that may be penetrated, upon user initiation, by the piercing member.

The novel embodiments of the present invention provide for user-initiated fluid pathway connections to drug containers, and drug pumps that utilize such connections and that are capable of maintaining the sterility of the fluid pathway before, during, and after operation of the device, and which enable active safety controls for the device.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1A:
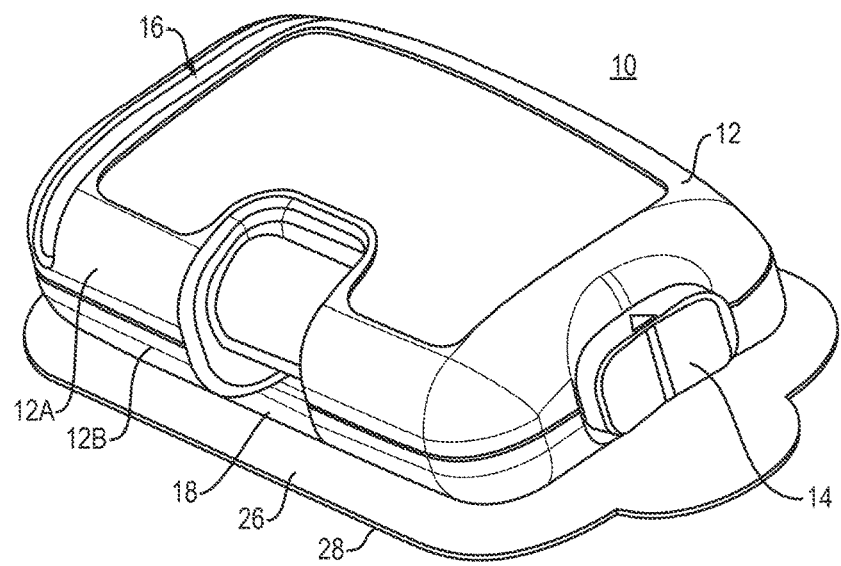
FIG. 1A shows an isometric view of a drug delivery pump having a sterile fluid pathway connect, according to one embodiment of the present invention.

A description of example embodiments follows.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" 15 refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the pumps. According to various aspects and embodiments described herein, reference is made to a "biasing member", which may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The novel devices of the present invention provide fluid pathway connections which are user-initiated and which maintain the aseptic condition of the fluid pathway, and drug delivery pumps which incorporate such aseptic fluid pathway connections to drug containers. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features while overcoming the problems associated with known prior art devices. Certain non-limiting embodiments of the novel drug delivery pumps, fluid pathway connections, and their respective components are described further herein with reference to the accompanying figures.

Conventional drug delivery devices often require filling at time-of-use because the terminal sterilization of the device cannot be completed with the pharmaceutical drug within the drug container. Various pharmaceutical drugs cannot withstand the temperatures, pressures, and other conditions necessary for sterilization of the device after assembly. In other words, because existing manufacturing processes require sterilization of the entire device, the drug cannot be "pre-filled" into the device prior to sterilization. This adds a complex step after final assembly of the device, which often requires costly additional equipment, handling of separate drug containers, and/or training of the patient to perform the filling step themselves prior to injection. Instead, the embodiments of the present invention enable the manufacture, assembly, and use of pre-filled drug delivery devices which maintain the sterility of the fluid pathway assembly through the various manufacturing steps.

Additionally, because the drug delivery devices which incorporate the novel embodiments of the present invention do not need to be terminally sterilized, the components of the devices may be constructed of other, often less expensive, materials which would not normally withstand the sterilization environment. For example, less expensive plastics may be utilized for certain device components because they do not need to be sterilized after assembly.

In other words, the embodiments of the present invention may allow the manufacturer to sterilize only the components which will be in contact with the drug fluid and/or which are necessary to maintain sterile fluid pathways. These embodiments may also allow the pharmaceutical filler to maintain the sterility of these components during the filling and finishing steps associated with the assembly of the drug delivery devices. Similarly, drug delivery devices which incorporate the fluid path connection mechanisms of the present invention may have smaller or more efficient geometries as the device does not have to be configured for sterilization after assembly.

Additionally, the embodiments of the present invention allow for the utilization of standard fill-finish processes to fill the drug container. This greatly simplifies the manufacturing processes used to build drug delivery devices. Standard fill-finish processes utilize trays which hold multiple drug containers, such as syringes. The embodiments of the present invention enable a drug delivery device manufacturer, pharmaceutical company, or contract drug filler to fill the drug containers for infusion or injection pumps using the same standard fill-finish processes. These drug containers can be filled aseptically, as is common industry practice, in a cost-efficient manner. After mounting of the fluid pathway connection mechanism the combined assembly can then be mated into a drug delivery device without requiring the remainder of the device components to be sterilized. Accordingly, embodiments of the present invention may provide novel components which enable the fluid pathway assemblies to be sterilized, assembled, filled, and incorporated into drug delivery devices in a cost-efficient and streamlined process.

In the processes of filling drug containers and other drug delivery devices, it is sometimes necessary to connect two or more sterile components or subassemblies. For example, wearable injectors or drug pumps may include a drug container, which may be filled with a fluid drug using standard aseptic pharmaceutical fill-finish processes. After filling of the drug container, it may be necessary to connect the drug container to one or more additional components or subassemblies such that a fluid communication may be established between the drug container and these components. Maintaining the fluid path in an aseptic condition is critical, preventing the introduction of harmful microbes to the drug and/or fluid pathway. The connection of two or more aseptic components or subassemblies is typically performed in an aseptic environment, thereby ensuring that no harmful foreign matter is introduced to the assembly. This, however, may lead to increased cost to manufacture the drug delivery devices. The fluid pathway connections of the present invention may be assembled to the drug container in a non-aseptic environment while maintaining the aseptic condition of the fluid path and drug fluid.

Figure 1B:
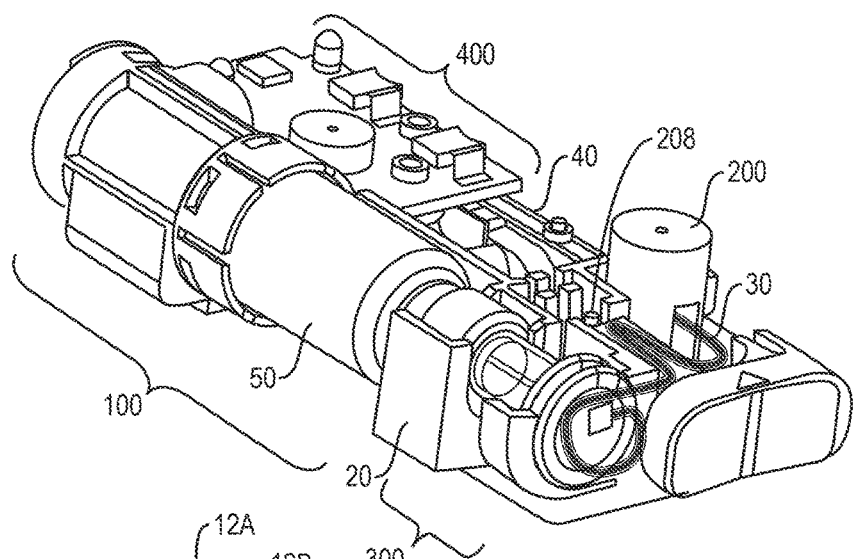
FIG. 1B shows an isometric view of the interior components of the drug delivery pump shown in FIG. 1A.
Figure 1C:
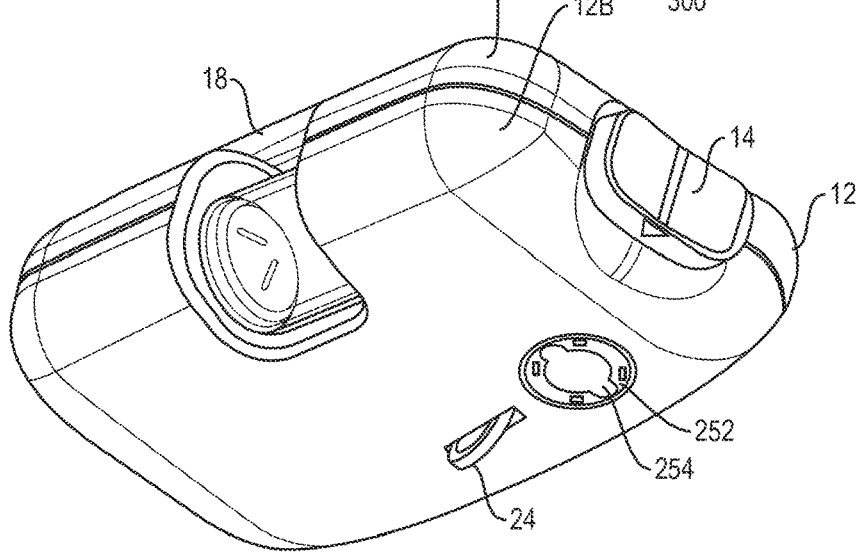
FIG. 1C shows an isometric view of the bottom of the drug delivery pump shown in FIG. 1A.

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes assembly platform 20, sterile fluid conduit 30, drive mechanism 100 having drug container 50, insertion mechanism 200, fluid pathway connection 300, and power and control system 400. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. For example, the drug pump can include an adhesive patch 26, which may initially be covered by a removeable, nonadhesive patch liner 28, for adhering the drug pump to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system 400. The activation mechanism, as shown in FIGS. 1A-1C, is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12 is described in further detail hereinafter with reference to other components and embodiments of the present invention.

The drug pump is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 1C) may be provided in one embodiment as a safety feature to ensure that the power and control system 400, or the activation mechanism, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12, which may be a transmissive or translucent material that permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

Other power and control system configurations may be utilized with the novel 10 drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Insertion Mechanism

A number of insertion mechanisms may be utilized within the drug pumps of the present invention. In at least one embodiment, the insertion mechanism 200 includes an insertion mechanism housing having one or more lockout windows, and a base 252 for connection to the assembly platform and/or pump housing (as shown in FIG. 1B and FIG. 1C). The connection of the base 252 to the assembly platform 20 may be, for example, such that the bottom of the base is permitted to pass-through a hole in the assembly platform to permit direct contact of the base to the body of the user. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit 30 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as a "trocars." In a preferred embodiment, the needle is a 27 gauge solid core trocar and in other embodiments, the needle may be any size needle suitable to insert the cannula for the type of drug and drug administration 10 (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 254 (shown in FIG. 1C).

According to at least one embodiment of the present invention, the insertion mechanism is initially locked into a ready-to use-stage by lockout pin(s) initially positioned within lockout windows of the insertion mechanism housing. In this initial configuration, insertion biasing member and retraction biasing member are each retained in their compressed, energized states. As shown in FIG. 1B, the lockout pin(s) 208 may be directly displaced by user depression of the activation mechanism 14. As the user disengages any safety mechanisms, such as an optional on-body sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows of the insertion mechanism housing. Displacement of the lockout pin(s) 208 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

Drive Mechanism

A number of drive mechanisms may be utilized to force fluid from a drug container for delivery into the body of a user. In one such embodiment, the drive mechanism 100 includes a drive housing, a status switch interconnect, and a drug container having a cap, a pierceable seal, a barrel, and a plunger seal. The drug container may contain a drug fluid, within the barrel between the pierceable seal and the plunger seal, for delivery through the insertion mechanism and drug pump into the body of the user. The seals described herein may be comprised of a number of materials but are, in a preferred embodiment, comprised of one or more elastomers or rubbers. The drive mechanism may further include a connection mount to guide the insertion of the piercing member of the fluid pathway connection into the barrel 58 (FIG. 2) of the drug container. The drive mechanism 100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connection, for delivery through the fluid pathway connection, sterile fluid conduit, and insertion mechanism into the body of the user.

In one particular embodiment, the drive mechanism 100 employs one or more compression springs as the biasing member(s). Upon activation of the drug pump by the user, the power and control system 400 may be actuated to directly or indirectly release the compression spring(s) from an energized state. Upon release, the compression spring(s) may bear against and act upon the plunger seal to force the fluid drug out of the drug container. The fluid pathway connection 300 may be connected through the pierceable seal prior to, concurrently with, or after activation of the drive mechanism to permit fluid flow from the drug container, through the fluid pathway connection, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

The components of the drive mechanism 100, upon activation, may be used to drive axial translation in the distal direction of the plunger seal of the drug container. Optionally, the drive mechanism 100 may include one or more compliance features which enable additional axial translation of the plunger seal to, for example, ensure that substantially the entire drug dose has been delivered to the user and make sure that the feedback contact mechanisms have connected. Additionally or alternatively, the plunger seal, itself, may have some compressibility permitting a compliance push of drug fluid from the drug container. The drive mechanism 100 may similarly include one or more status indication mechanisms, such as interconnects and contacts, to measure and communicate the status of the drive mechanism before, during, and after operation of the drive mechanism and the device to the user. Furthermore, the drive mechanism 100 may include one or more safety mechanisms, such as premature activation prevention mechanisms, to enhance the safety and usability of the mechanism and the device. Further details related to the drive mechanism 100 are provided herein with reference to other components of the drug pump.

Fluid Pathway Connection

Figure 2:
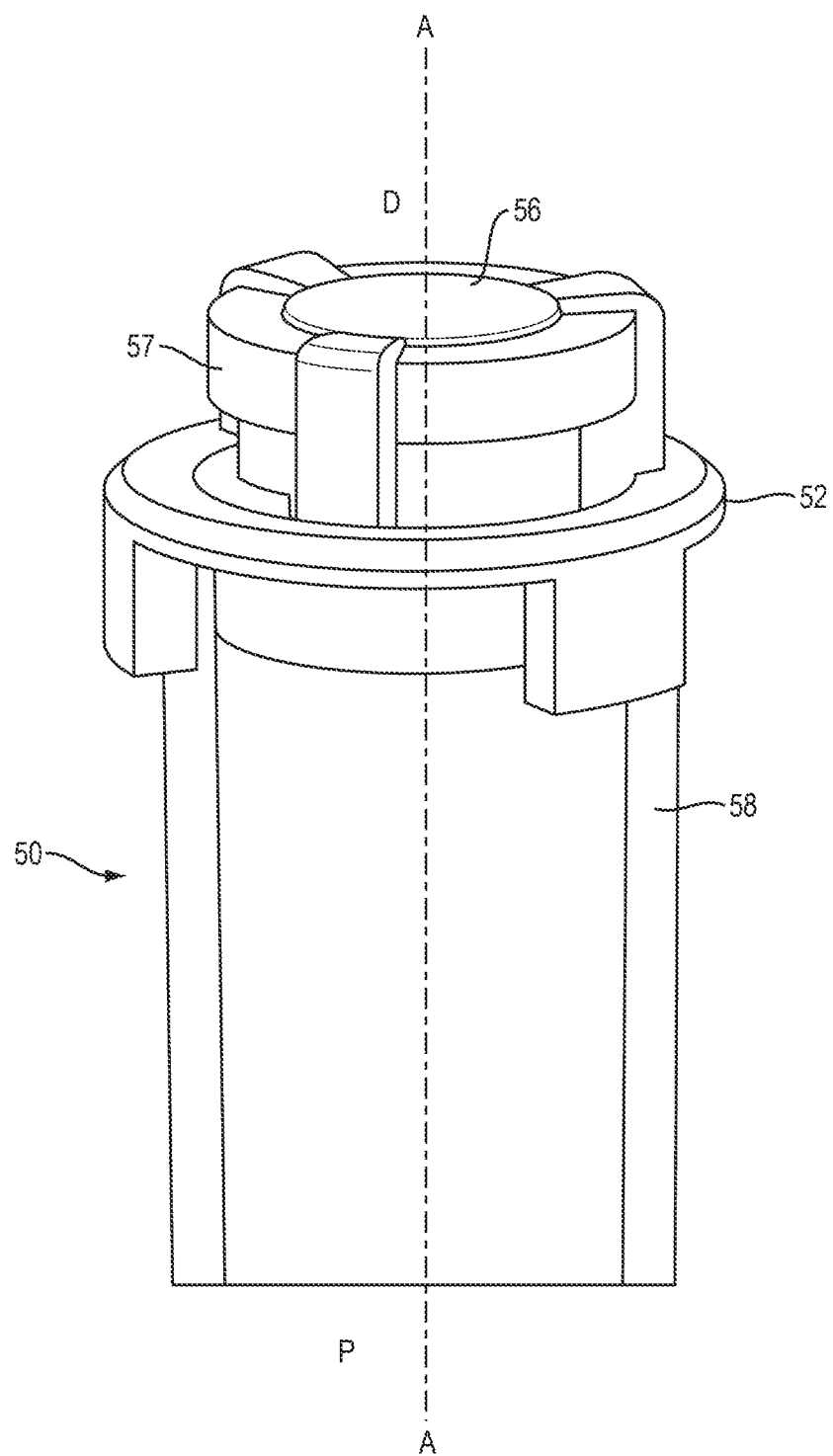
FIG. 2 shows an isometric view of a drug container according to at least one embodiment of the present invention.
Figure 3:
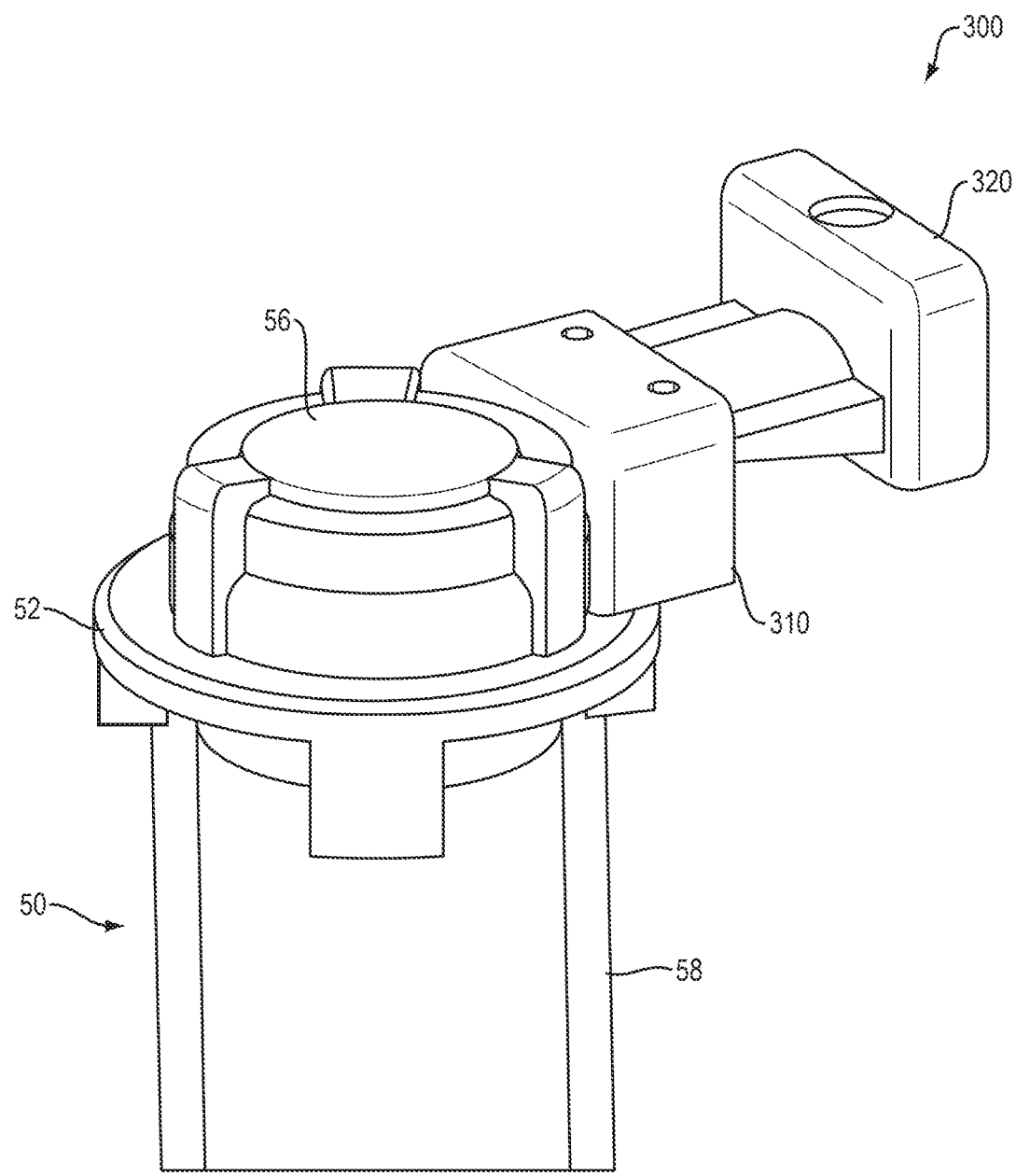
FIG. 3 shows an isometric view of a drug container and a fluid pathway connection according to at least one embodiment of the present invention.

As shown in the embodiment of FIGS. 2-4, the drug container 50 includes barrel 58, cap 52, and pierceable seal 56. Base 56A of pierceable seal 56 may be in sealing engagement with the inside of barrel 58. Cap 52 may be fixedly engaged to the outside of barrel 58 and may retain pierceable seal 56 in position and restrict movement of pierceable seal 56 with respect to barrel 58. Cap 52 may include one or more locking arms 52A which extend from ring 52B of cap 52 substantially parallel to axis A-A and in a distal direction. The locking arms 52A may include a radially extending protrusion 52C at or near their distal ends. The drug container may further include toroidal seal 57. In an initial configuration, shown in FIGS. 2, 4A, and 4B, the toroidal seal 57 is retained between protrusions 52C and proximal circumferential rib 56B of pierceable seal 56. Pierceable seal 56 may further include distal circumferential rib 56C which further retains toroidal seal 57. By placing the toroidal seal in this position when the drug container is in an aseptic environment the portion of pierceable seal 56 in contact with the inner face of toroidal seal 57 (e.g., as depicted in FIG. 4B, the area between the proximal circumferential rib and the distal circumferential rib) is maintained in an aseptic condition, even if the drug container is moved to a septic environment.

Figure 4A:
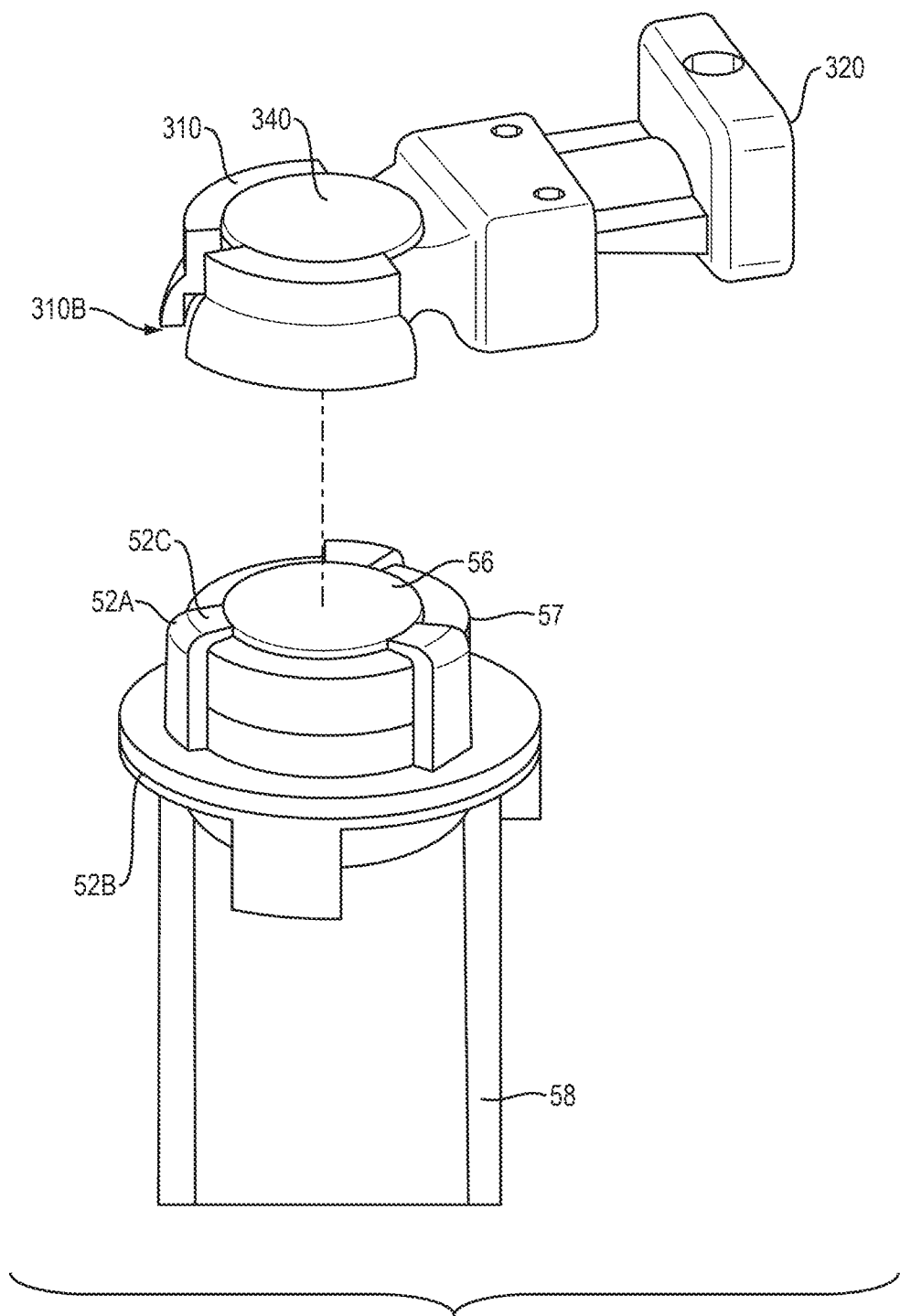
FIG. 4A shows an isometric view of the drug container and fluid pathway connection of FIG. 3 in an unmounted configuration.
Figure 4B:
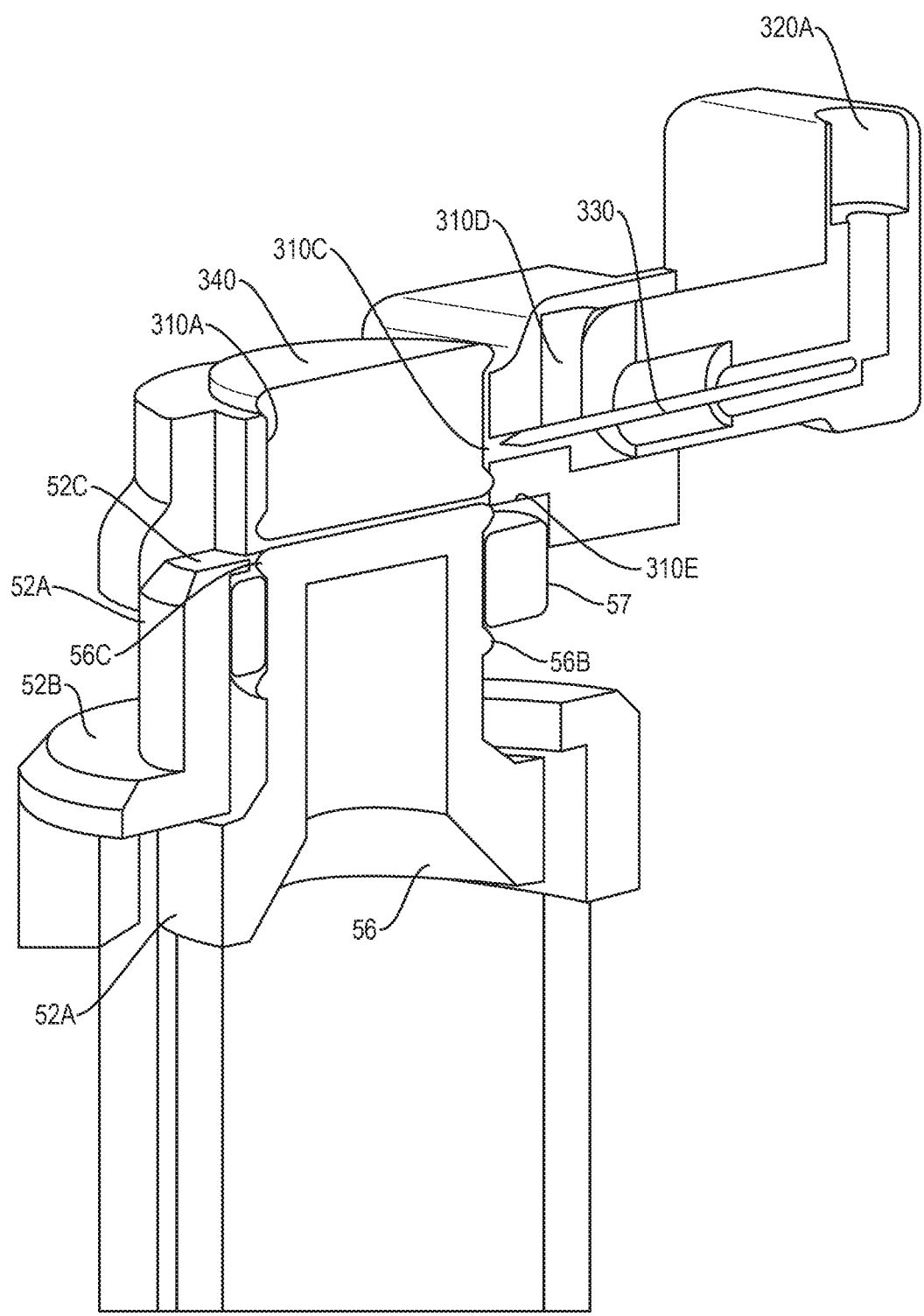
FIG. 4B shows a cross-sectional isometric view of the drug container and fluid pathway connection of FIG. 3 in an initial mounting configuration.

The fluid pathway connection 300 includes connection hub 310, retainer 320, piercing member 330, and plug seal 340. As shown in FIGS. 4A-4B, plug seal 340 is initially disposed within bore 310A of connection hub 310. When the fluid pathway connection is assembled, the plug seal maintains the aseptic condition of at least a portion of the fluid pathway connection by maintaining a sealing engagement with bore 310A. The retainer is disposed for sliding translation with respect to connection hub 310 in a direction parallel to axis B-B (shown in FIG. 4D). Initially, translation of retainer 320 may be restricted. The restriction may be by engagement of flex arms 320B with recesses in connection hub 310. Piercing member 330 may be fixedly engaged with retainer 320 such that translation of retainer 320 is transferred to the piercing member. The piercing member may be bonded, press-fit, or engaged to the retainer using other appropriate means. The piercing member may initially be at least partially disposed within cavity 310D and/or aperture 310C of connection hub 310. The cavity 310D and/or aperture 310C of the connection hub are alternatively referred to, individually or collectively, as a sterile chamber in which at least a portion of piercing member 330 resides. Cavity 310D and aperture 310C are maintained in an aseptic condition by plug seal 340. Retainer 320 may further include conduit connection 320A to which a sterile fluid conduit 30 may be attached. This provides a sterile fluid path from the sterile fluid pathway connection to the insertion mechanism. Piercing member 330 may be a hollow needle, such that fluids can pass through the hollow interior of the piercing member and into the sterile fluid conduit.

FIGS. 4A-4D show the steps of connecting the fluid pathway connection 300 to the drug container 50. This connection may be performed in a non-aseptic environment.

Figure 4C:
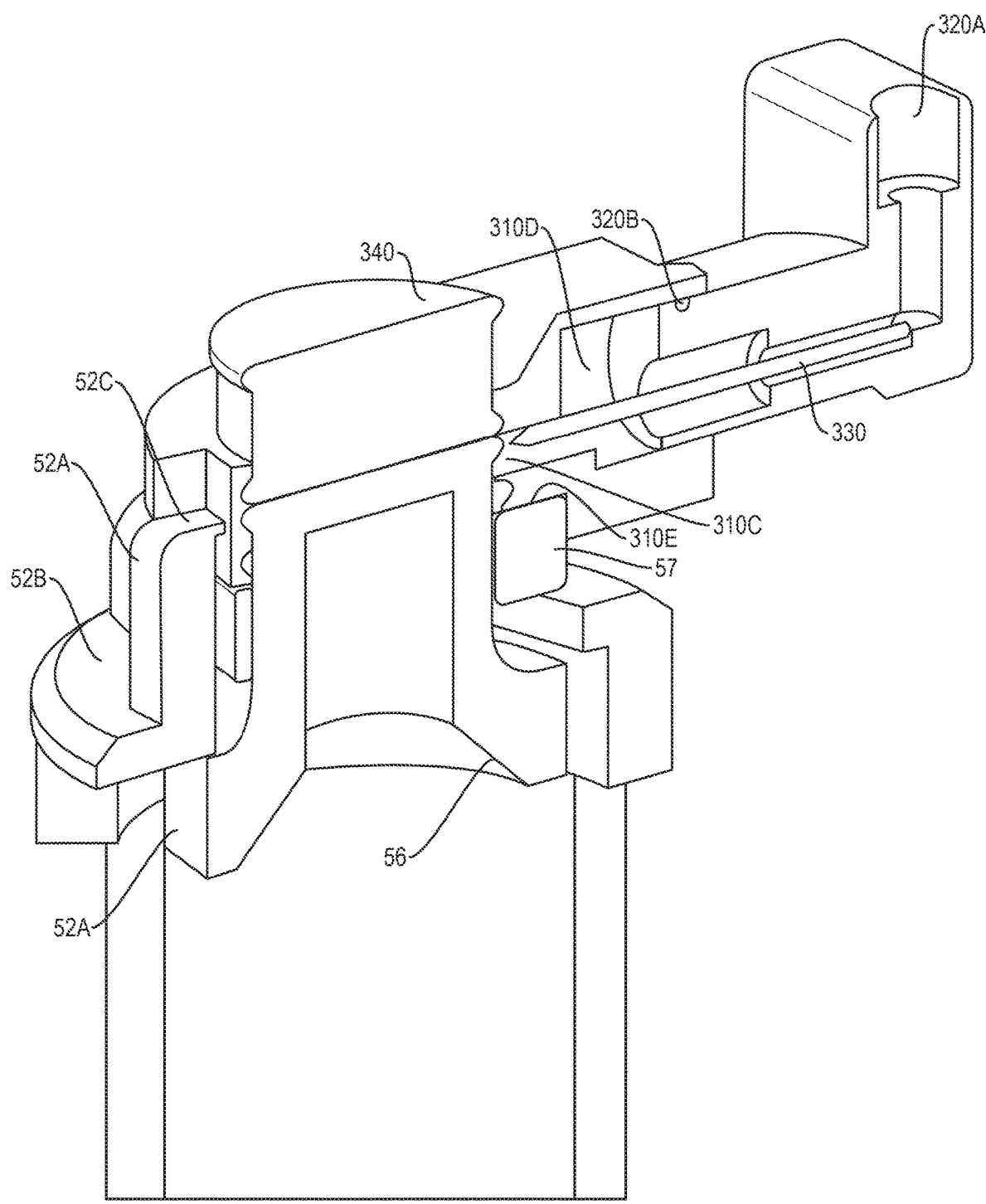
FIG. 4C shows a cross-sectional isometric view of the drug container and fluid 10 pathway connection of FIG. 3 in an intermediate mounting configuration.

In FIG. 4A, the plug seal of the fluid pathway connection is substantially aligned with axis A-A (i.e., the plug seal 340 is aligned with the distal end of the pierceable seal 56). FIG. 4B shows a cross-section view of the fluid pathway connection 300 in contact with the drug container. Recesses 310B of connection hub 310 are aligned with locking arms 52A, this alignment guides the installation of the fluid pathway connection and prevents rotation of the fluid pathway connection with respect to the drug container. As shown in FIG. 4C, as the connection hub is translated in the proximal direction along axis A-A the plug seal 340 is prevented from translating with the connection hub due to contact with pierceable seal 56. This causes the plug seal to be displaced from its position within bore 310A. Additionally, contact of shoulder 310E of connection hub 310 with toroidal seal 57 causes the toroidal seal to translate in the proximal direction along axis A-A. As the connection hub is translated along axis A-A only bore 310A comes in contact with the portion of the pierceable seal which was previously covered by toroidal seal 57. Further, as the connection hub comes into contact with the toroidal seal these components sealingly engage such that microbes and other foreign substances may not come in contact with the sterile portions of the pierceable seal and fluid pathway connection. In this way the aseptic condition of the pierceable seal 56, aperture 310C, cavity 310D, and piercing member 330 are maintained during installation of the fluid pathway connection.

Figure 4D:
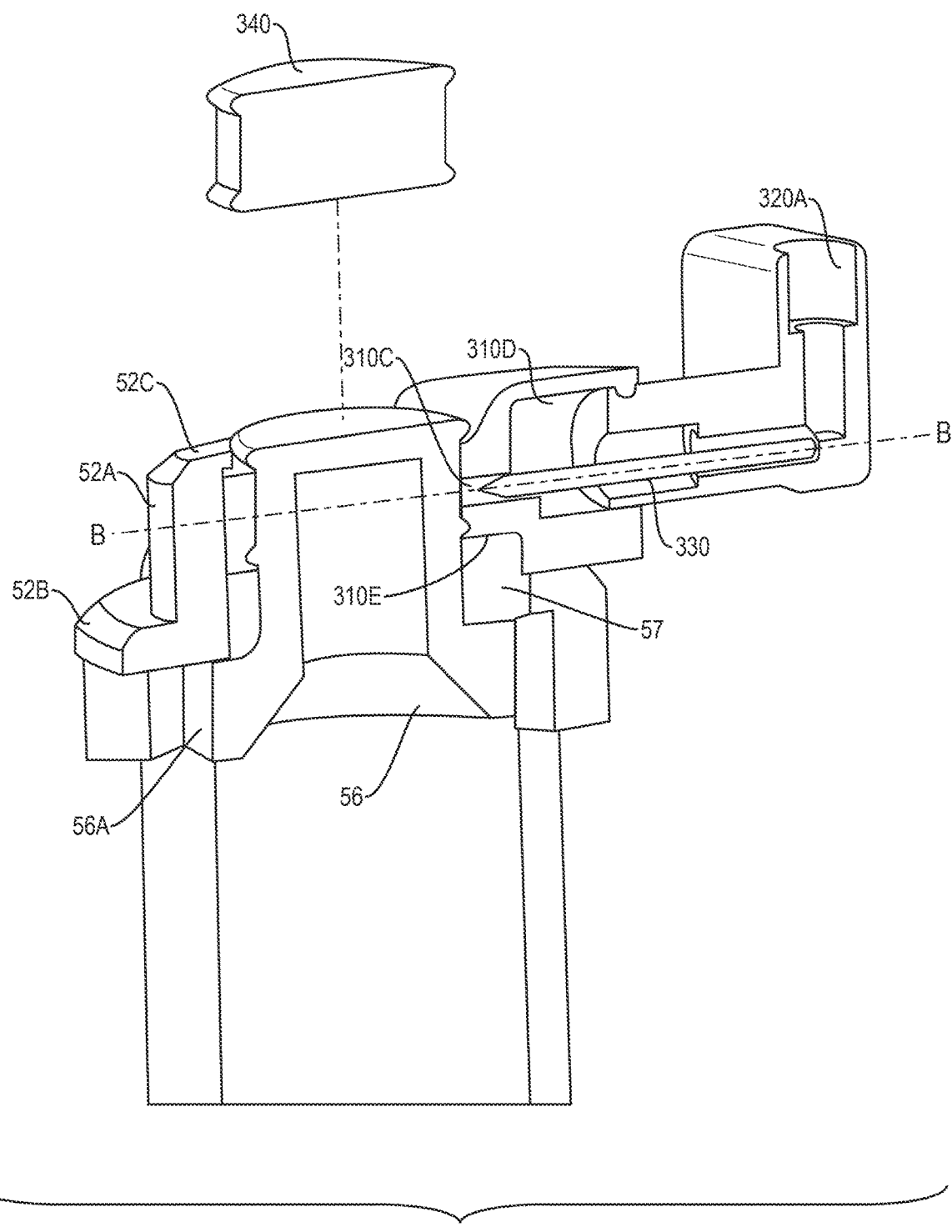
FIG. 4D shows a cross-sectional isometric view of the drug container and fluid pathway connection of FIG. 3 in a mounted configuration.

As seen in FIG. 4D, further proximal translation of the connection hub brings the connection hub into contact with a portion of drug container 50, thus preventing further distal translation of the connection hub. In the embodiment shown, the connection hub contacts a portion of cap 52. When the connection hub reaches this position, the plug seal may be removed from the assembly and discarded. Snap arms 52A may engage one or more aspects of the connection hub and thereby prevent the connection hub from being removed from the drug container.

After installation, the piercing member is aligned with the sterile portion of the pierceable seal that was originally engaged with the toroidal seal. The components may be assembled into drug pump 10 and remain in this configuration until activation of the drug pump by the user. Upon activation, the retainer 320 is translated in a direction parallel to axis B-B with respect to the connection hub, causing translation of piercing member 330. Due to this translation, the piercing member comes in contact with and, subsequently, pierces the pierceable seal 56. This opens a fluid pathway from the drug container and through the piercing member. The fluid pathway may further include a sterile fluid conduit 30 that is engaged with conduit connection 320A of retainer 320. In this way, a sterile fluid path is provided from the drug container to the insertion mechanism for delivery to the patient.

Figure 5A:
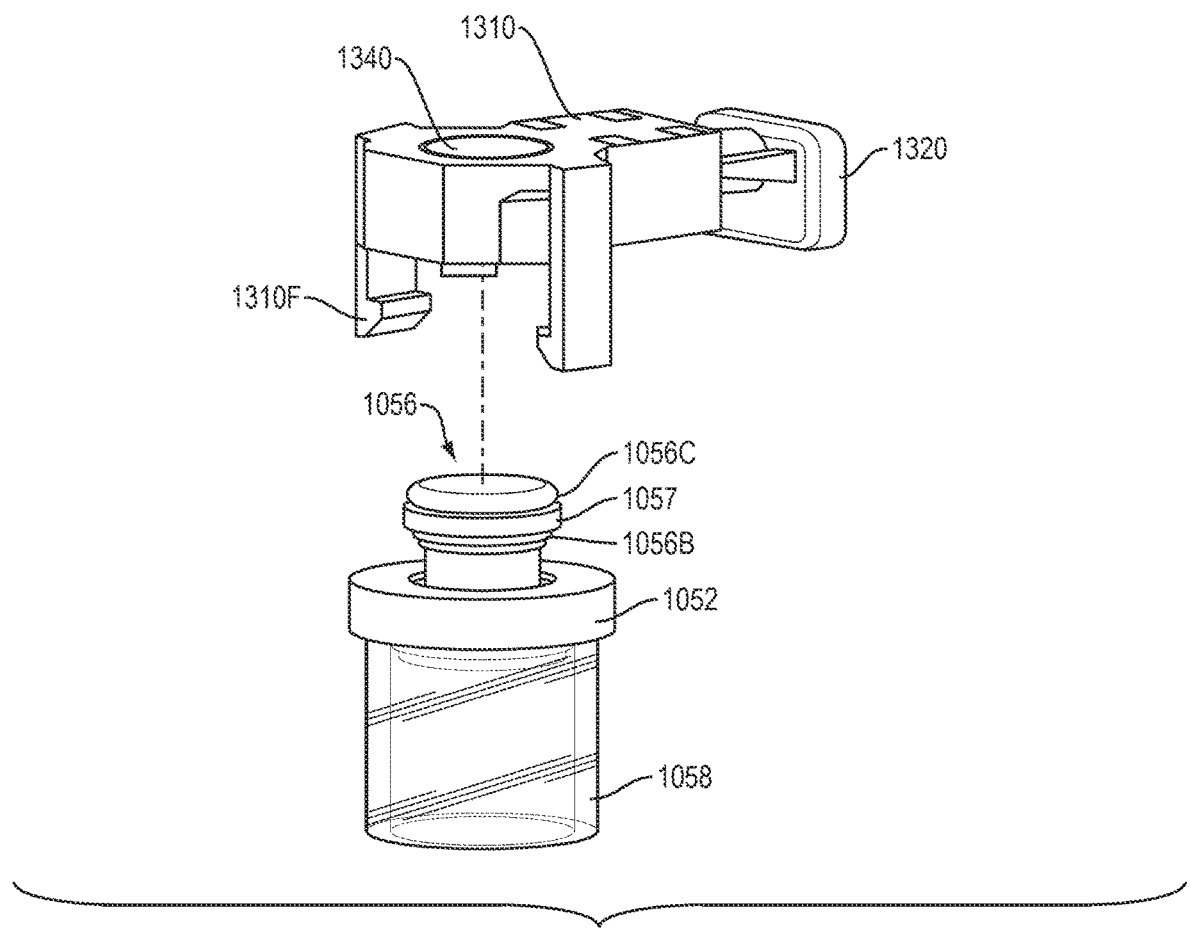
FIG. 5A shows an isometric view of an embodiment of a drug container and fluid pathway connection in an unmounted configuration.
Figure 5B:
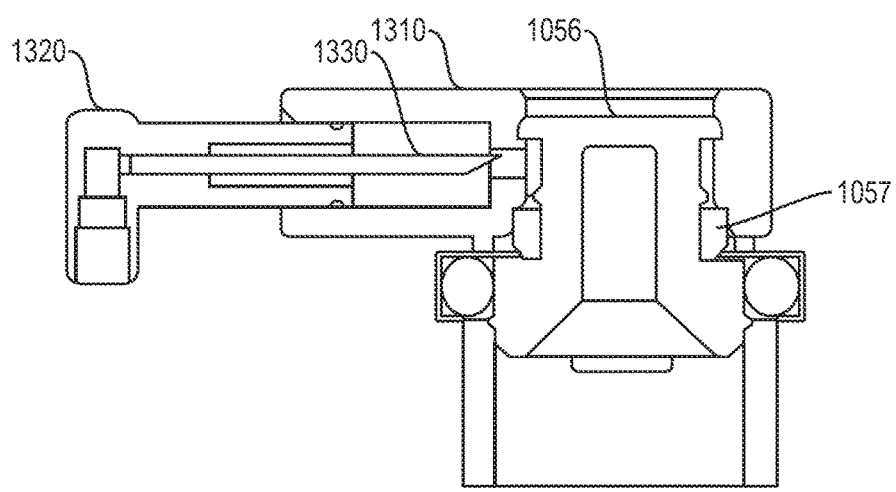
FIG. 5B shows a cross-sectional isometric view of the drug container and fluid pathway connection of FIG. 5A in a mounted configuration.

FIGS. 5A-5B show another embodiment of the present invention in which connection hub 1310 includes snap arms 1310F, which may engage cap 1052 of drug container 1050 or the drug container barrel 1058. Toroidal seal 1057 is initially retained between proximal circumferential rib 1056B and distal circumferential rib 1056C of pierceable seal 1056 and is caused to translate in the proximal direction by contact with the connection hub. Connection hub also includes plug seal 1340 and needle retainer 1320. After mounting of the fluid pathway connection to the drug container, opening of the fluid pathway is substantially similar as that described above, in which plug seal 1340 is displaced from the connection hub 1310 and needle retainer 1320 is able to translate to cause a piercing member 1330 to pierce the pierceable seal 1056.

Figure 6:
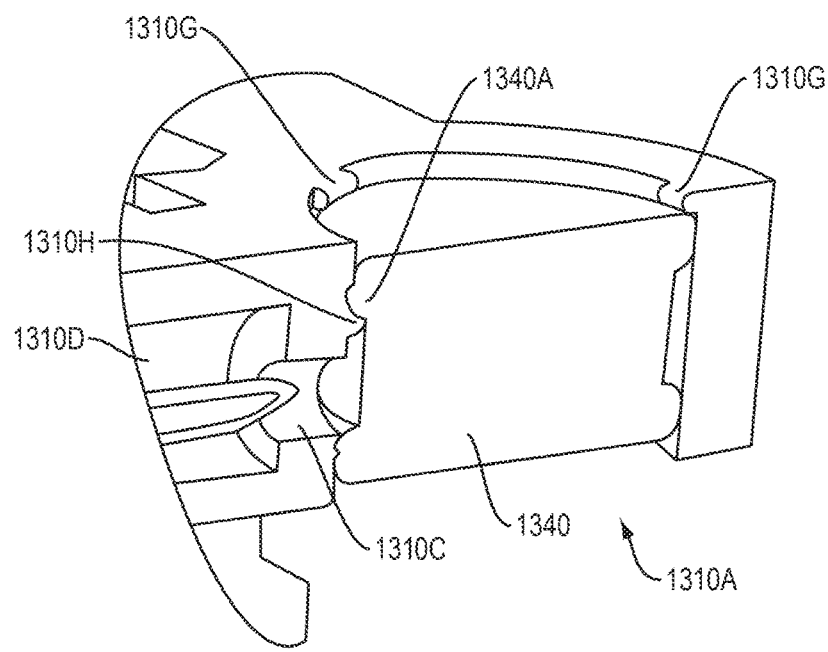
FIG. 6 shows a detail cross-sectional view of a fluid pathway connection according to at least one embodiment of the present invention.

FIG. 6 shows a detail view of a plug seal 1340 disposed within a bore 1310A of a connection hub. This shows a possible method of, and features for, retaining the plug seal 1340 in an initial position using tabs 1310G and/or tabs 1310H. The tabs 1310G can control the location of the plug seal in the inner bore, and cause plug seal 1340 to be retained in a position such that cavity 1310D and aperture 1310C are sealed. Tabs 1310H can cooperate with a circumferential rib 1340A to further retain the plug seal at a location within the bore. As illustrated, one or more tabs 1310G, 1310H can be included in a connection hub, and one or more circumferential ribs 1340A can be included in a plug seal.

Figure 7:
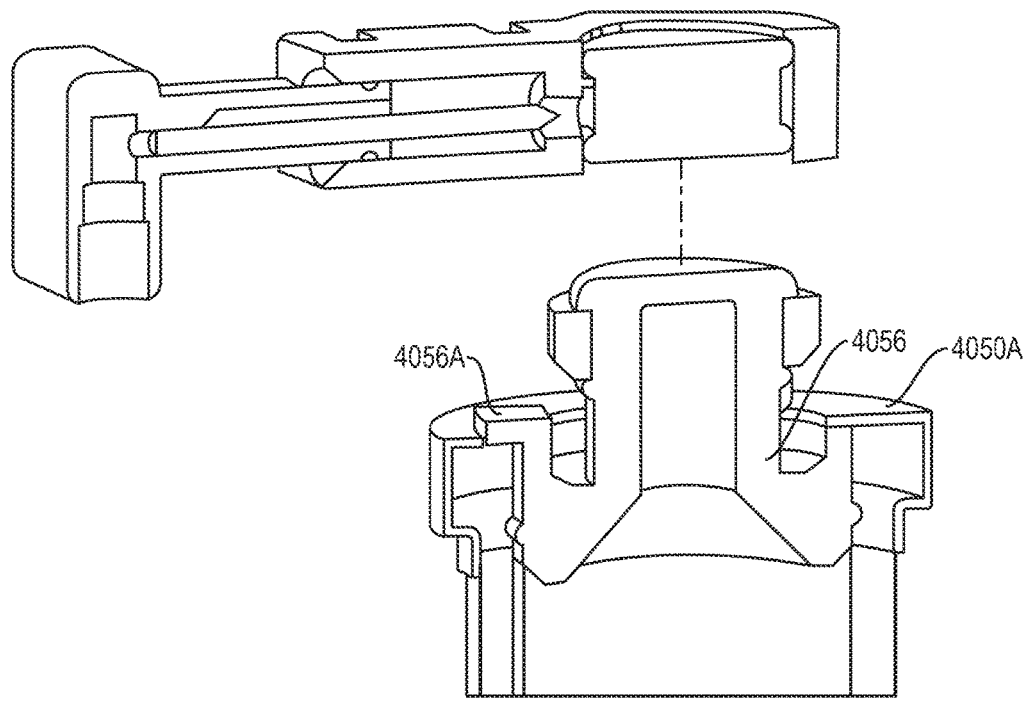
FIG. 7 shows a cross-sectional isometric view of an embodiment of a drug container and fluid pathway connection in an unmounted configuration.
Figure 8:
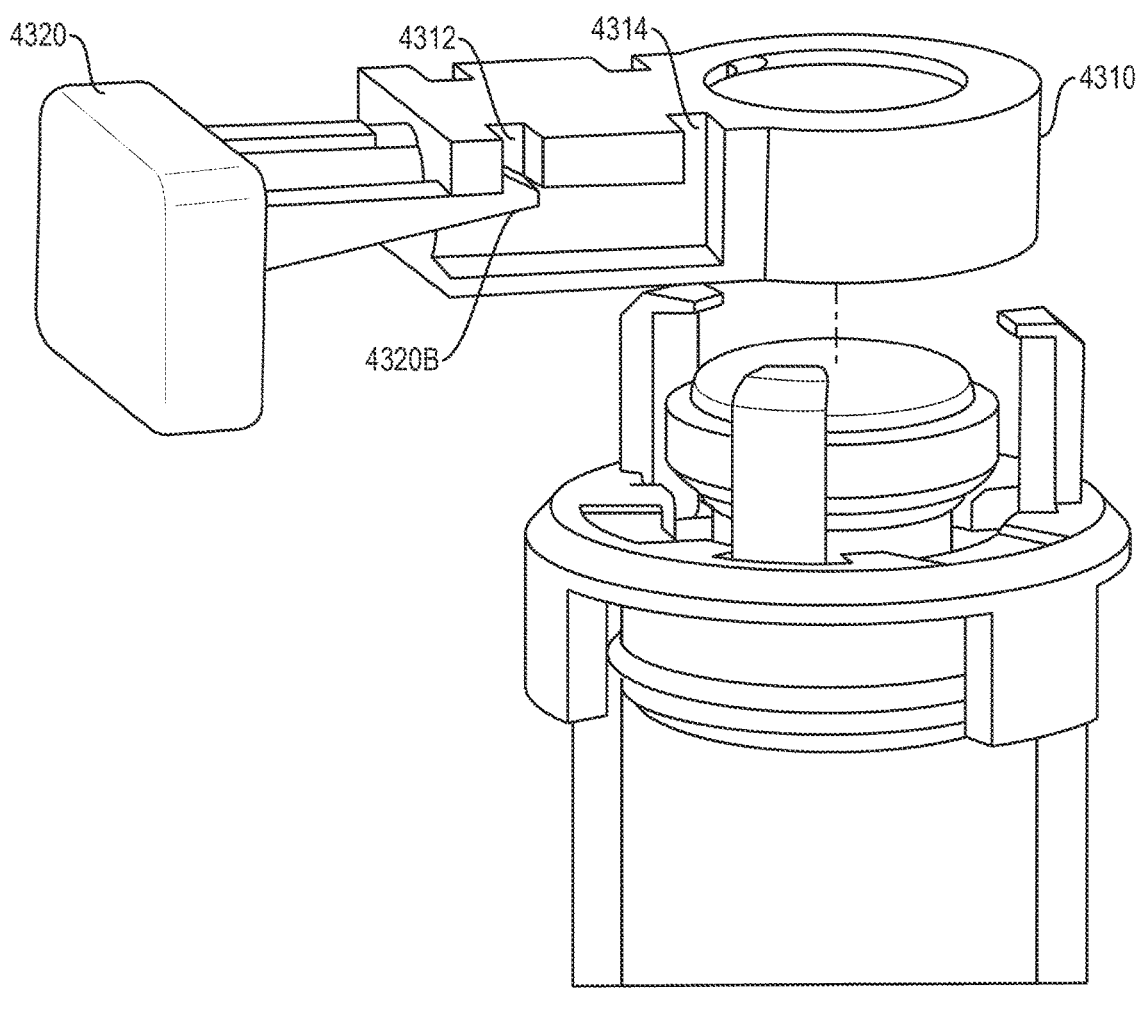
FIG. 8 shows an isometric view of an embodiment of a drug container and fluid pathway connection in an unmounted configuration.
Figure 9:
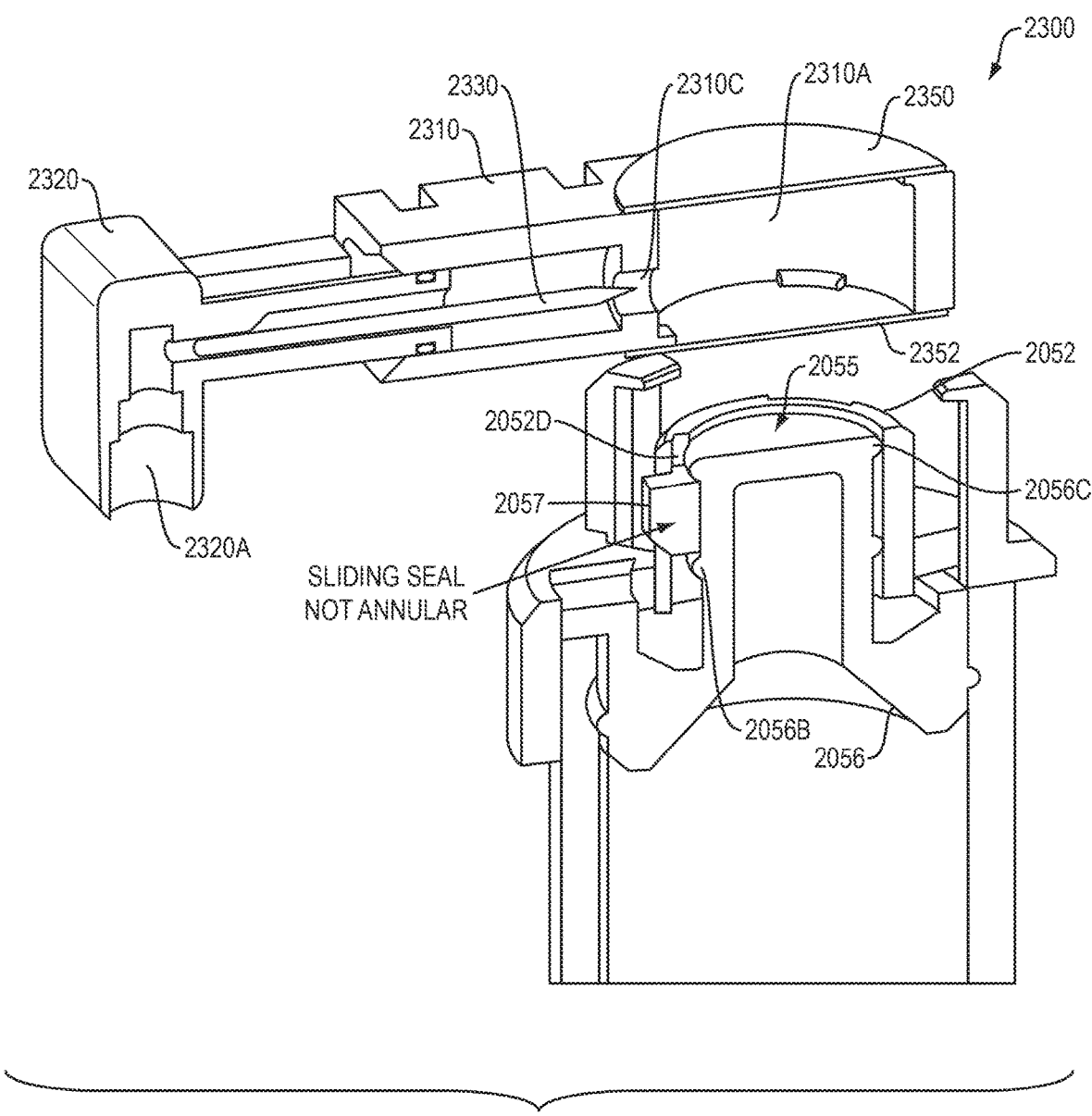
FIG. 9 shows a cross-sectional isometric view of an embodiment of a drug container and fluid pathway connection in an unmounted configuration.

FIGS. 7-9 show additional, alternative configurations of a cap and a pierceable seal. As shown in FIG. 7, a projection 4056A of the pierceable seal 4056 rests against a surface 4050A of a drug container, which can prevent the pierceable seal from collapsing inwards to the drug container prior to or during connection with a connection hub. As best shown in FIG. 8, needle retainer 4320 can be initially prevented from translation with respect to connection hub 4310 through engagement of flex arms 4320B with recesses 4312. During activation of the drug pump, needle retainer 4320 can be configured to translate upon application of a force that causes flex arms 4320 to disengage from recesses 4312. Optionally, upon translation, flex arms 4320B may engage with secondary recesses 4314 to prevent the needle retainer 4320 from translating in an opposite direction. One or more flex arms 4320B and/or one more recesses 4312, 4314 can be included.

In the embodiment shown in FIG. 9, a bore 2310A of connection hub 2310 is enclosed on its distal face by distal film 2350 and on its proximal face by proximal film 2352. The proximal and distal films may be constructed from any material with barrier properties sufficient to prevent the passage of foreign matter. For example, the films may be constructed from a foil material. The films may be bonded or otherwise securely affixed to the connection hub. In this way, bore 2310A is maintained in an aseptic condition.

As the fluid pathway connection is brought into contact with the drug container, a portion of the drug container pierces, tears, or otherwise removes a portion of proximal film 2352 from the connection hub. For example, as shown in FIG. 9, a portion of the cap 2052 contacts the proximal film during installation and disengages a portion thereof from the connection hub. The disengaged portion of proximal seal 2352 may be retained within a void 2055 formed by cap 2052 and pierceable seal 2056, thereby preventing the septic portion of proximal film 2352 from contacting the aseptic portion of pierceable seal 2056.

Also shown in FIG. 9, a sliding seal 2057 may be configured to maintain the aseptic condition of only a portion of the circumference of pierceable seal 2056. This portion may be configured to be aligned with aperture 2310C and piercing member 2330 after installation of fluid pathway connection 2300. During installation, seal 2057 is displaced by the connection hub as described in reference to other embodiments. Seal 2057 may be retained in position with respect to the pierceable seal by engagement of the seal with slot 2052D of cap 2052, proximal circumferential rib 2056B, and distal circumferential rib 2056C. During displacement, the seal may translate within slot 2052D in the proximal direction. After mounting of the fluid pathway connection to the drug container, opening of the fluid pathway is substantially similar as that described above, in which needle retainer 2320 is able to translate to cause a pierceable member 2330 to pierce the pierceable seal 2056 and conduit connection 2320A is configured to be connected to a fluid conduit for drug delivery to a patent.

FIGS. 10A-10D show another embodiment of a fluid pathway connection 3300 in which the fluid pathway connection includes first rotating disk 3360 and drug container 3050 includes second rotating disk 3051. First rotating disk 3360 may be configured for rotation with respect to connection hub 3310 about a central axis and further include first opening 3360A. As shown in FIG. 11A, the first rotating disk may also include post 3360B and receptacle 3360C. Second rotating disk 3051 may include complementary features to allow for alignment of the first opening 3360A with the second opening 3051A. Second rotating disk 3051 may be configured for rotation with respect to the drug container and have second opening 3051A. One or both of the openings may initially be covered by a film such that the film prevents foreign materials from entering the openings.

Figure 10A:
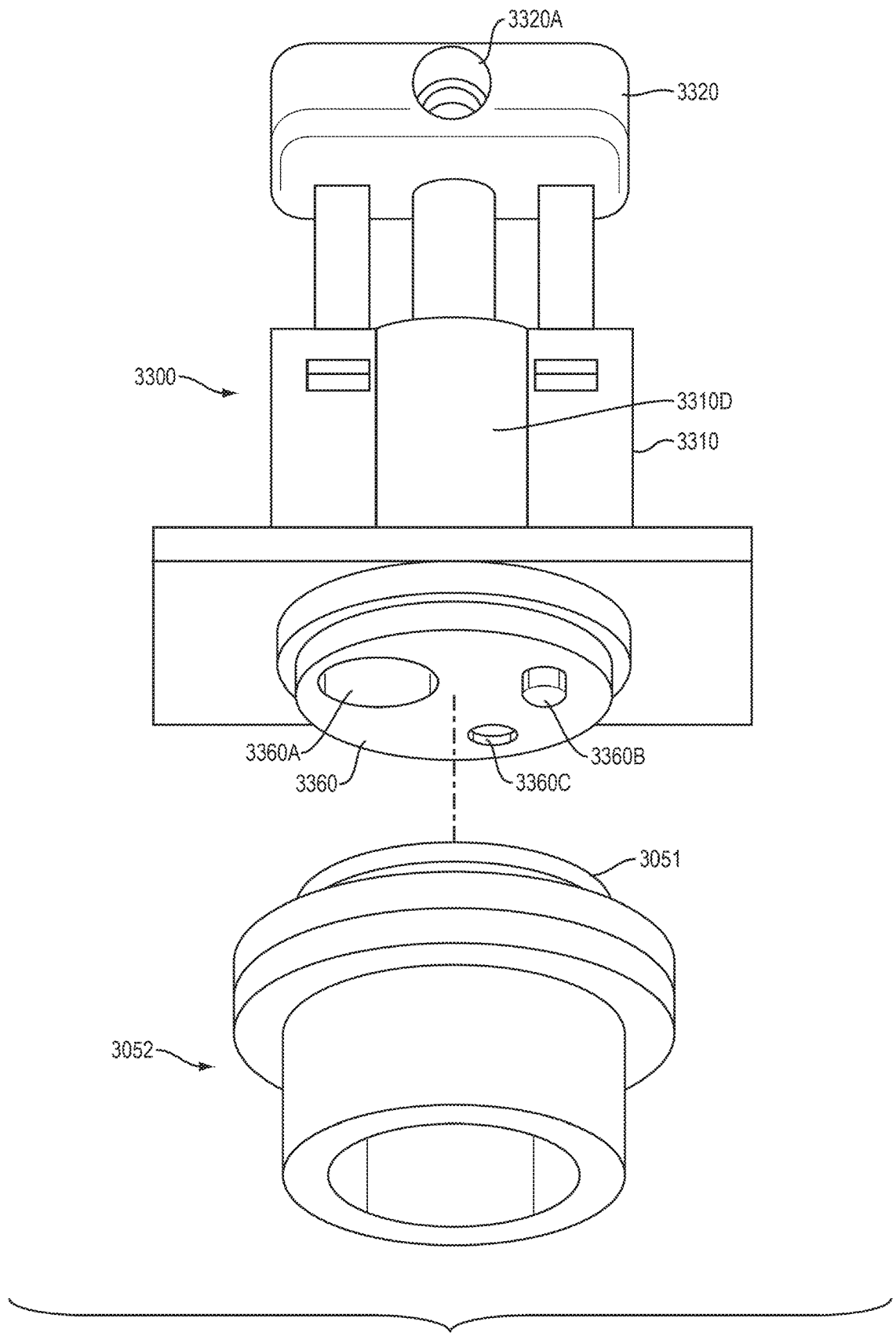
FIG. 10A shows an isometric view of an embodiment of a drug container and fluid pathway connection in an unmounted configuration.
Figure 10B:
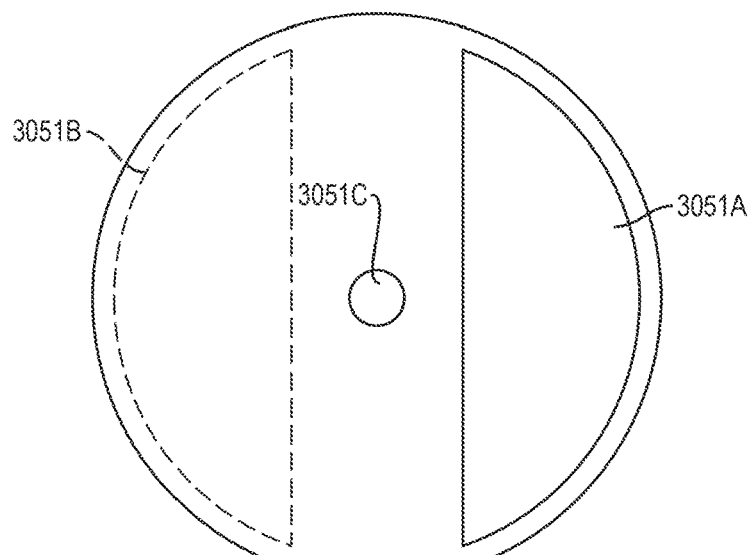
FIG. 10B shows an end view of a drug container.

First opening 3360A is shown in FIG. 10A to be a substantially circular opening, however other shapes for openings 3360A, 3051A are possible. As shown in FIG. 10B, illustrating an end view of the drug container 3050 with cap 3052, opening 3051A is substantially hemispherical. The relative location of a fourth opening 3051B at the top of the drug container, covered by the second rotating disk 3051, is shown in a dashed line in FIG. 10B. The rotating disks may be caused to rotate about a central axis of the drug container and connection member, such as around an axial feature 3051C, such as a shaft.

Figure 10C:
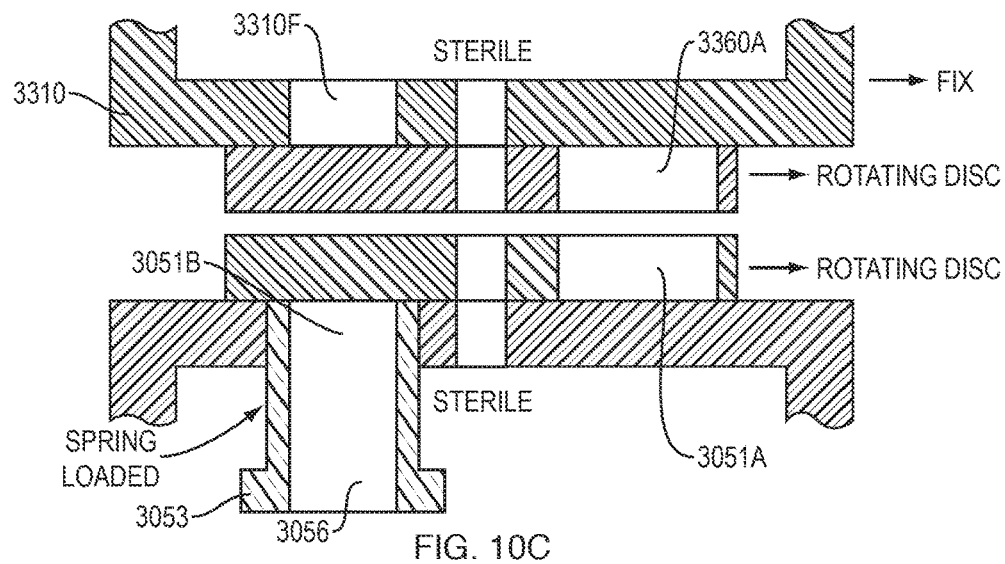
FIG. 10C shows a cross-sectional view of a drug container and fluid pathway connection in an unmounted configuration.
Figure 10D:
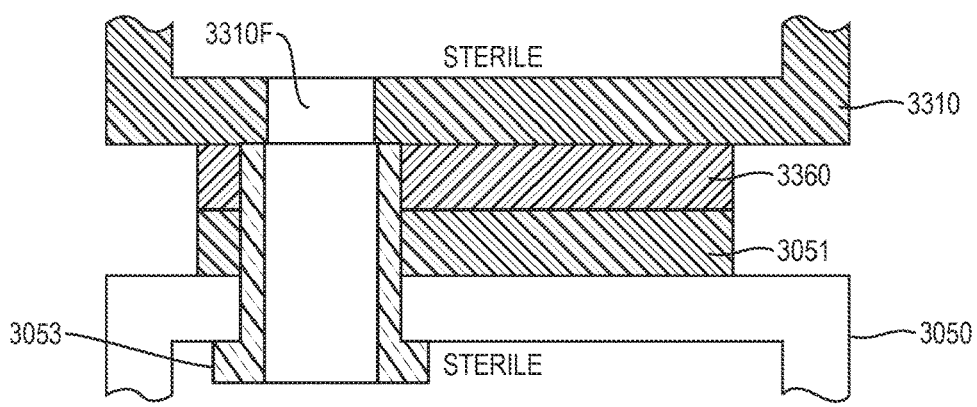
FIG. 10D shows a cross-sectional view of a drug container and fluid pathway connection in a connected configuration.

As seen in FIG. 10C, during installation the first and second rotating disks are brought into contact such that the first and second openings are aligned. The rotating disks may be joined through the use of an adhesive or, alternatively, may be held in contact by features, such as the snap arms described previously in relation to other embodiments or by snap-fit engagement between posts and receptacles located on the rotating disks. Once connected, the disks may be rotated such that they align with a fourth opening, 3051B, which can optionally be defined by a chimney 3053, and third opening 3310F in connection hub 3310. Chimney 3053 may be biased for axial movement in the distal direction, such as by a spring or other biasing member capable of storing energy. As shown in FIG. 10D, upon alignment with the first and second opening, the chimney translates in the distal direction, passing through both the first and second openings. The chimney may have a pass-through which allows contents to flow from the drug container. In this way, a sterile fluid path is created between the drug container and the fluid pathway connection. Optionally, the fluid pathway connection may further include a piercing member which is configured to, upon activation by a user, pass through the chimney and pierce a pierceable seal 3056 of the drug container. As shown in FIG. 10C, a pierceable seal 3056 is located at a base of chimney 3053, however one or more pierceable seals may be included at any of the openings 3051A, 3051B, 3310A, 3310F. After the pierceable seal is pierced, drug fluid may pass from a chamber 3310D defined by the connection hub 3310, through the piercing member, and be delivered to the patient. The piercing member may be engaged with retainer 3320. The retainer may also be configured for connection of sterile fluid conduit 30 at conduit connection 3320A. The translation of the piercing member may be caused by translation of the retainer 3320 with respect to the connection hub 3310.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A fluid pathway connection, comprising:
   a connection hub defining a bore and including a seal configured to maintain an aseptic condition of the bore;
   a piercing member;
   a piercing member retainer; and
   a drug container including a cap, a pierceable seal, and a barrel, wherein the piercing member is at least partially disposed in a sterile chamber defined by the connection hub and the connection hub is configured to be connected to the drug container while maintaining an aseptic condition of a fluid pathway from the sterile chamber to an interior of the drug container, the seal of the connection hub configured to be displaced by the pierceable seal of the drug container.

2. The fluid pathway connection of claim 1, wherein the bore is configured to receive the pierceable seal of the drug container.

3. The fluid pathway connection of claim 1, wherein the seal is a plug seal initially disposed within the bore.

4. The fluid pathway connection of claim 1, wherein the seal is a film seal initially disposed at an opening of the bore.

5. The fluid pathway connection of claim 1, wherein the drug container further comprises a sliding seal, the sliding seal initially sealingly engaged with at least a portion of the pierceable seal.

6. The fluid pathway connection of claim 5, wherein the sliding seal is configured to translate upon the pierceable seal upon connection of the connection hub with the drug container.

7. The fluid pathway connection of claim 5, wherein the pierceable seal includes at least one circumferential rib configured to retain the sliding seal in an initial position.

8. The fluid pathway connection of claim 5, wherein the sliding seal is a toroidal seal.

9. The fluid pathway connection of claim 1, wherein the piercing member retainer is translatable with respect to the connection hub.

10. The fluid pathway connection of claim 9, wherein the piercing member is configured to pierce the pierceable seal upon translation of the piercing member retainer.

11. The fluid pathway connection of claim 1, wherein the cap includes at least one locking arm configured to engage with the connection hub.

12. The fluid pathway connection of claim 1, wherein the connection hub includes at least one locking arm configured to engage with the cap.

13. The fluid pathway connection of claim 1, wherein the drug container contains a drug fluid.

14. A drug delivery pump, comprising:
   a housing;
   an activation mechanism;
   a power and control system;
   a drive mechanism; and
   a fluid pathway connection, comprising:
      a connection hub defining a bore and including a seal configured to maintain an aseptic condition of the bore,
      a piercing member,
      a piercing member retainer, and
      a drug container including a cap, a pierceable seal, and a barrel, wherein the piercing member is at least partially disposed in a sterile chamber defined by the connection hub and the connection hub is configured to be connected to the drug container while maintaining an aseptic condition of a fluid pathway from the sterile chamber to an interior of the drug container, the seal of the connection hub configured to be displaced by the pierceable seal of the drug container.

15. The drug delivery pump of claim 14, further comprising an assembly platform upon which the activation mechanism, power and control system, drive mechanism, and fluid pathway connection are mounted.

16. The drug delivery pump of claim 14, wherein the fluid pathway connection is in fluid communication with a fluid conduit, the fluid pathway connection and the fluid conduit defining a sterile fluid path from the fluid pathway connection to an insertion mechanism.

17. A method of assembling a fluid pathway connection, comprising:
aligning a bore of a connection hub with a pierceable seal of a drug container, the drug container further including a cap and a barrel, and the connection hub further including a seal configured to maintain an aseptic condition of the bore and a sterile chamber in which a piercing member is disposed;
translating the connection hub onto the cap of the drug container, the seal of the connection hub being displaced by the pierceable seal.

18. The method of claim 17, wherein the seal of the connection hub is a plug seal and wherein translating the connection hub onto the cap includes displacing the plug seal from the bore of the connection hub.

19. The method of claim 17, wherein the seal of the connection hub is a film seal and wherein translating the connection hub onto the cap includes displacing the film seal from an opening of the bore of the connection hub.

20. The method of claim 17, wherein translating the connection hub onto the cap includes displacing a sliding seal located at the pierceable seal.

21. The method of claim 17, further comprising translating a piercing member retainer, the piercing member piercing the pierceable seal upon translation of the piercing member retainer.

* * * * *